US010414655B2

(12) United States Patent
Bosnyak et al.

(10) Patent No.: US 10,414,655 B2
(45) Date of Patent: *Sep. 17, 2019

(54) STEM CELL, BONE, TISSUE AND NERVE SCAFFOLDING FROM DISCRETE CARBON NANOTUBES

(71) Applicant: MOLECULAR REBAR DESIGN, LLC, Austin, TX (US)

(72) Inventors: Clive P. Bosnyak, Dripping Springs, TX (US); Kurt W. Swogger, Austin, TX (US); Nancy Henderson, Austin, TX (US); Paul Everill, Austin, TX (US)

(73) Assignee: Molecular Rebar Design, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/778,444

(22) PCT Filed: Apr. 7, 2017

(86) PCT No.: PCT/US2017/026696
§ 371 (c)(1),
(2) Date: May 23, 2018

(87) PCT Pub. No.: WO2017/177193
PCT Pub. Date: Oct. 12, 2017

(65) Prior Publication Data
US 2018/0339904 A1 Nov. 29, 2018

Related U.S. Application Data

(60) Provisional application No. 62/319,599, filed on Apr. 7, 2016.

(51) Int. Cl.
| | |
|---|---|
| *A61K 47/02* | (2006.01) |
| *A61K 9/00* | (2006.01) |
| *C01B 32/16* | (2017.01) |
| *C02F 1/28* | (2006.01) |
| *C01B 32/168* | (2017.01) |
| *C01B 32/174* | (2017.01) |
| *C01B 32/178* | (2017.01) |
| *B82Y 30/00* | (2011.01) |
| *B82Y 40/00* | (2011.01) |
| *C02F 103/06* | (2006.01) |
| *C02F 101/30* | (2006.01) |
| *C02F 101/36* | (2006.01) |
| *B82Y 5/00* | (2011.01) |

(52) U.S. Cl.
CPC ............ *C01B 32/16* (2017.08); *A61K 9/0092* (2013.01); *A61K 47/02* (2013.01); *C01B 32/168* (2017.08); *C01B 32/174* (2017.08); *C01B 32/178* (2017.08); *C02F 1/283* (2013.01); *A61K 9/0019* (2013.01); *B82Y 5/00* (2013.01); *B82Y 30/00* (2013.01); *B82Y 40/00* (2013.01); *C01B 2202/06* (2013.01); *C01B 2202/34* (2013.01); *C01B 2202/36* (2013.01); *C02F 2101/30* (2013.01); *C02F 2101/36* (2013.01); *C02F 2103/06* (2013.01); *C02F 2305/08* (2013.01); *Y10S 977/744* (2013.01); *Y10S 977/748* (2013.01); *Y10S 977/752* (2013.01); *Y10S 977/846* (2013.01); *Y10S 977/847* (2013.01); *Y10S 977/903* (2013.01); *Y10S 977/906* (2013.01)

(58) Field of Classification Search
CPC .............. A61K 9/703; A61K 47/48776; A61K 9/0092; A61K 47/02; C01B 32/16
See application file for complete search history.

(56) References Cited

U.S. PATENT DOCUMENTS

| | | |
|---|---|---|
| 2003/0153827 A1 | 8/2003 | Ritter et al. |
| 2004/0267362 A1 | 12/2004 | Hwang et al. |
| 2007/0154552 A1 | 7/2007 | Siegal et al. |
| 2009/0148417 A1 | 6/2009 | Kim et al. |
| 2015/0182473 A1* | 7/2015 | Bosnyak ................ A61K 9/703 514/356 |
| 2015/0238476 A1* | 8/2015 | Bosnyak ................ A61K 9/703 424/400 |

OTHER PUBLICATIONS

Rajesh et al. "Development of a new carbon nantube-alginate-hydroxyapatite tricomponent composite scaffold for application in bone tissue engineering", International J of Nanomedicine, Oct. 2015, 7-15 (Year: 2015).*
U.S. Appl. No. 14/628,248 (Year: 2015).*
Int'l Search Report & Written Opinion (PCT/US2017/026696), dated Jun. 27, 2017.

* cited by examiner

*Primary Examiner* — Ruth A Davis
(74) *Attorney, Agent, or Firm* — Stephen P. Krupp

(57) ABSTRACT

Stem cell, bone and nerve scaffolding comprising discrete carbon nanotubes is disclosed. The discrete carbon nanotubes may be have targeted, or selective oxidation levels and/or content on the interior and exterior of the tube walls. The described scaffolding may be used to guide, target and protect stem cells upon injection into the body.

28 Claims, No Drawings

STEM CELL, BONE, TISSUE AND NERVE SCAFFOLDING FROM DISCRETE CARBON NANOTUBES

CROSS REFERENCE TO RELATED APPLICATIONS

The present application claims priority from U.S. application Ser. No. (USSN) 62/319,599 filed on Apr. 7, 2016, the entire disclosure of which is incorporated herein by reference.

FIELD OF THE INVENTION

The present invention relates to a discrete carbon nanotube scaffold for transplanting a stem cell and a composition for stem cell therapy. The invention also relates to discrete carbon nanotube scaffolding for bone, tissue and nerve growth and repair.

BACKGROUND AND SUMMARY OF THE INVENTION

Multipotent stem cells have become highlighted as therapeutic agents for ischemia, Parkinson's disease, Alzheimer's disease, cardiac infarction, and liver diseases. Stem cells transplanted become effective in treatment of diseases only if the following requirements are met: The first requirement is that stem cells transplanted are differentiated into a cell type of interest. The second requirement is to form networks between differentiated stem cells and surrounding tissues and cells. Regenerative tissue or bone structures involve directed growth of cells to form higher order structures.

However, in the practical realm, stem cells transplanted in injured region are very likely to be washed away with no formation of networks (e.g., neuron networks). To make matters worse, they can migrate to an undesirable region and differentiated into undesirable cell types such as tumors.

Accordingly, there have been made extensive researches to develop scaffolds without in vivo toxicities for stem cell. However, the development of scaffolds without toxicities has been considered a difficult task and the injection of scaffolds into body has been frequently reported to cause adverse effects. Significant issues can arise with carbon nanotubes that have toxic metal elements or salts that come from residual catalysts, such as Cobalt, used to make the carbon nanotubes, clumps or bundles of carbon nanotubes that cannot be used to make scaffolds of uniform structure, and hydrophobic surfaces that do not allow ease of affinity with stem cells and products of their differentiation.

Therefore, there remains a need to develop a novel scaffold having convenient and more effective clinical applicability with no in vivo toxicities.

Throughout this application, several patents and publications are referenced and citations are provided. The disclosure of these patents and publications is incorporated into this application in order to more fully describe this invention and the state of the art to which this invention pertains. A review of several studies is provided in "Carbon Nanotubes for Stem Cell Control". D. A. Stout and T. J. Webster. Materials Today, July-August 2012, Volume 15, Number 7-8, pp. 312-318, Elsevier.

The present inventors have discovered that a plurality of discrete carbon nanotubes offer novel capabilities to specifically locate and create scaffolds for stem cells without cytotoxicity, thereby allowing networking between differentiated stem cells and tissues present in sites, and hence significant cell therapy efficacy. Cytotoxicity is herein defined as the quality of causing significant or undesirable harm to healthy cells. Without cytotoxicity indicates that significant portions of beneficial cells are not deleteriously affected, killed, or both as a direct result of the scaffolding or composition.

An embodiment of this invention is that the discrete carbon nanotubes in the scaffolding further comprise an amount of functional groups of at least about 1 percent by weight of the dry discrete carbon nanotubes. A plurality of discrete carbon nanotubes can be open ended and substantially cleaned of catalytic residues.

Another embodiment of this invention are scaffold comprising discrete carbon nanotubes, wherein the discrete carbon nanotubes have a length less than 4 micrometers, preferably less than 3 micrometers and more preferably less than 2 micrometers. The length distribution of discrete carbon nanotubes can have a modality, preferably monomodal, most preferably bimodal.

In yet another embodiment of this invention the scaffold further comprises a polymer. The polymer can be selected from a group of polymers that do not exhibit cytotoxity or incite immune response. The polymer may also be selected from a group of polymers that are biodegradable and or water soluble. The polymer further comprises the weight percentage range of about 1 to about 99, preferably less than about 90 percent, more preferably less than about 50 percent and most preferably less than about 10 percent of the scaffold.

A further embodiment of this invention is the discrete carbon nanotubes of the scaffolding further comprise functional groups that increase affinity of biological moieties to the discrete carbon nanotube surface.

A yet further embodiment of this invention is a composition for stem cell therapy, which comprises: (a) a stem cell; and (b) discrete carbon nanotubes serving as a stem cell scaffold without cytotoxicity. The stem cell may be an embryonic stem cell or adult stem cell. The stem cell can also be neuronal stem cell and the composition is one for treating neuronal diseases. The neuronal disease may be selected from the group consisting of neurodegenerative disorder. The neurodegenerative disorder can be selected from the group consisting of Alzheimer's disease, Huntington's disease, Parkinson's disease, motor neuron disease and amyotrophic lateral sclerosis.

Another embodiment of this invention is the composition for stem cell therapy wherein the discrete carbon nanotube is in the form of suspension.

A further embodiment of this invention is a cell therapy method using a stem cell, which comprises administering to an animal a composition for stem cell therapy comprising (a) a stem cell; and (b) discrete carbon nanotubes serving as a stem cell scaffold without cytotoxicity. The stem cell can be an embryonic stem cell or adult stem cell. The stem cell can also be neuronal stem cell and the composition is one for treating neuronal diseases. The neuronal disease may be selected from the group consisting of neurodegenerative disorder. The neurodegenerative disorder can be selected from the group consisting of Alzheimer's disease, Huntington's disease, Parkinson's disease, neural motor disease and amyotrophic lateral sclerosis. The discrete carbon nanotube can be in the form of a suspension.

An additional embodiment of this invention is the use of a composition comprising (a) a stem cell; and (b) discrete carbon nanotubes serving as a stem cell scaffold without cytotoxicity for manufacturing a medicament for cell therapy. The stem cell can be an embryonic stem cell or adult stem cell. The stem cell can also be neuronal stem cell and the composition is one for treating neuronal diseases. The neuronal disease may be selected from the group consisting of neurodegenerative disorder and ischemia-reperfusion injury. The neurodegenerative disorder can be selected from the group consisting of Alzheimer's disease, Huntington's disease, Parkinson's disease and amyotrophic lateral sclerosis. The ischemia-reperfusion injury can be an ischemic stroke. The discrete carbon nanotube can be in the form of a suspension.

It is another object of this invention to provide a composition comprising (a) a stem cell; and (b) discrete carbon nanotubes serving as a stem cell scaffold without cytotoxicity for manufacturing a medicament for cell therapy wherein the scaffold and stem cell for stem cell therapy further comprise a medicant.

Another object of this invention is to provide a composition comprising (a) a stem cell; and (b) discrete carbon nanotubes serving as a stem cell scaffold without cytotoxicity wherein the scaffold is in the form of a foam, fiber or film. The scaffold may further comprise a multilayer.

An additional object of this invention is to provide discrete carbon nanotubes within the scaffold wherein the discrete carbon nanotubes have a least a portion of the discrete carbon nanotubes that are oriented.

Another object of this invention is to provide a method to protect stem cells from damage by encasing the stem cell into a scaffold comprising discrete carbon nanotubes.

An embodiment of this invention is a method to protect stems cells from damage during injection or deposition by encasing the stem cell into a scaffold comprising discrete carbon nanotubes.

Another embodiment of this invention is a composition comprising (a) a stem cell; and (b) discrete carbon nanotubes serving as a stem cell scaffold without cytotoxicity further comprising an inducer for stem cell differentiation.

A further embodiment of this invention is a method to form a stem cell scaffold by admixing a mixture of discrete nanotubes with different functionalities wherein on mixing the nanotubes associate with each other type of functionality.

A yet further embodiment of this invention is a stem cell scaffold comprising discrete carbon nanotubes, and further comprising a surfactant. The surfactant can be anionic, cationic or non-ionic.

Another embodiment of this invention is a stem cell scaffold comprising discrete carbon nanotubes that can be used as an adhesive for tissue, or bone.

In yet another embodiment of this invention the scaffold further comprises a polymer wherein the polymer is selected from a group of biological polymers comprising proteins, peptides, long chain carbohydrates, proteoglycans, or lipids. The polymer can be partly digested or modified. The components of the polymer can be substantially similar to the make-up of the extracellular matrix or an antibody locking the scaffold to lesions or sites of cell damage.

In an additional embodiment of this invention the scaffold further comprises a polymer wherein the polymer is selected from a group of biological polymers comprising chemotactic, wound healing, extracellular matrix producing proteins. The extracellular producing protein can further comprise fibronectin, integrin, or fibrin.

DETAILED DESCRIPTION OF THE INVENTION

In the following description, certain details are set forth such as specific quantities, sizes, etc. so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not, unless specifically stated in this specification or if the incorporation is necessary for maintaining validity.

A discrete carbon nanotube, DCNT, serving as stem cell scaffold used in this invention can consist of single wall, double wall or multiwall graphene shells.

The term "Discrete Carbon Nanotubes (DCNT)" means carbon nanotubes that are unbundled or untangled from their state as made in the reactor with catalysis and do not require further cutting of their length to be able to be substantially separated from one another along the length of the carbon nanotube. The discrete carbon nanotubes can be individually dispersed in a given medium by selection of the thermodynamic interaction of the tube surface and the medium and the tube concentration. For example, discrete carbon nanotubes of this invention can be dispersed easily at a concentration of 1% by weight in water using 0.5% by weight of polyvinyl alcohol of molecular weight about 50,000 Daltons.

During the process of making discrete or exfoliated carbon nanotubes (which can be single, double and multi-wall configurations), from bundles or entangled masses of carbon nanotubes, the nanotubes are cut into segments with at least one open end and residual catalyst particles that are interior to the carbon nanotubes as received from the manufacturer are removed. This cutting of the tubes helps with exfoliation. The cutting of the tubes reduces the length of the tubes into carbon nanotube segments that are defined here as Molecular Rebar. Proper selection of the carbon nanotube feed stock related to catalyst particle type and distribution in the carbon nanotubes allows more control over the resulting individual tube lengths and overall tube length distribution. A preferred selection is where the internal catalyst sites are evenly spaced and where the catalyst is most efficient. A further preferred selection is where there are Stones-Wales defects present along the wall or walls of the carbon nanotube. Individual discrete carbon nanotubes can have an aspect ratio of from about 10 to about 500, preferably 25-200 and most preferably 50-120 for a balance of fluid viscosity and performance. The selection of tubes for the scaffold can be evaluated using electron microscopy and determination of the discrete or exfoliated tube distribution.

Discrete oxidized carbon nanotubes, alternatively termed exfoliated carbon nanotubes, are obtained from as-made bundled or entangled carbon nanotubes by such methods as involving oxidation, such as using a combination of concentrated sulfuric and nitric acids. The bundled or entangled carbon nanotubes can be made from any known means such as, for example, chemical vapor deposition, laser ablation, and high pressure carbon monoxide synthesis. It is preferred that the carbon nanotubes are made via catalysts that are non-toxic, for example iron. The bundled carbon nanotubes can be present in a variety of forms including, for example, soot, powder, fibers, and bucky paper. Furthermore, the bundled carbon nanotubes may be of any length, diameter, or chirality. Carbon nanotubes may be metallic, semi-metallic, semi-conducting, or non-metallic based on their chirality and number of walls. The discrete oxidized carbon nanotubes may include, for example, single-wall, double-wall carbon nanotubes, or multi-wall carbon nanotubes and combinations thereof. One of ordinary skill in the art will recognize that many of the specific aspects of this invention illustrated utilizing a particular type of carbon nanotube may be practiced equivalently within the spirit and scope of the disclosure utilizing other types of carbon nanotubes.

A preferred selection of carbon nanotubes of this invention is the incorporation of a portion of structures called Stone-Wales defects which are the rearrangement of the six-membered rings of graphene into heptagon-pentagon pairs that fit within the hexagonal lattice of fused benzene rings constituting a wall of the carbon nanotubes. These Stone-Wales defects are useful to create sites of higher bond-strain energy for more facile reaction such as oxidation of the graphene or carbon nanotube wall. These defects and other types of fused ring structures may also facilitate bending or curling along the length of the carbon nanotubes which is advantageous for maintaining fluidity of mixtures of discrete carbon nanotubes with fluids at higher concentrations of discrete carbon nanotubes.

Stone-Wales defects are thought to be more prevalent at the end caps that allow higher degrees of curvature of the walls of carbon nanotubes. During oxidation the ends of the carbon nanotubes can be opened and also result in higher degrees of oxidation than along the walls. The higher degree of oxidation and hence higher polarity or hydrogen bonding at the ends of the tubes are useful to help decrease the average contour length to end to end ratio when the tubes are present in polar media such as water.

According to a preferred embodiment, the discrete carbon nanotubes are functionalized. The functional groups linked to DCNT include, but not limited to, hydroxyl, thiol, amide, amine and carboxyl groups. The functionalized DCNT allows for the decrease in aggregation between DCNT molecules in a medium and greater affinity of stem cells and other biological moieties. The functionalization allows for interaction with inorganic metals, inorganic salts, organic molecules such as, but not limited to polyethylene glycol, and biological species such as, but not limited to DNA, RNA, peptides, proteins and enzymes. Functionalized carbon nanotubes of the present disclosure generally refer to the chemical modification of any of the carbon nanotube types described hereinabove. Such modifications can involve the nanotube ends, sidewalls, or both. Chemical modifications may include, but are not limited to covalent bonding, ionic bonding, chemisorption, intercalation, surfactant interactions, polymer wrapping, cutting, solvation, and combinations thereof.

Surfactants can be usefully employed also to modify the thermodynamic interactions between the tubes and the medium of choice. Alternate means to influence the ratio of discrete carbon nanotube contour length to end to end ratio include the use of inorganic or ionic salts such as sodium chloride and organic containing functional groups such as polyethylene oxide or polyvinyl alcohol that can be attached to or contacted with the tube surfaces.

The discrete carbon nanotubes can be oriented, although not limited, by extrusion through a circular or slit die. The orientation is facilitated by the presence of a polymer in the fluid. An example of this is employing discrete carbon nanotubes of this invention in the presence of polyvinyl alcohol and water such that polyvinyl alcohol-oriented discrete carbon nanotube fibers can be obtained by electrospinning or via orifices in the wall of a spinning centrifuge.

The discrete carbon nanotubes used in the invention described herein need not comprise 100% discrete carbon nanotubes. That is, some tube bundles may still exist as entangled, non-discrete tubes. However, the carbon nanotubes used in this scaffolding invention comprise at least 70% (wt. based on the whole nanotube compositions) of discrete carbon nanotubes, more preferably greater than 80%, most preferably greater than 95% and especially 99% or more discrete carbon nanotubes.

The stem cell scaffold comprising discrete carbon nanotubes can further comprise polymers. The polymers may vary in concentration relative to the discrete carbon nanotubes in the weight percentage range of about 1 to about 99, preferably less than about 90 percent, more preferably less than about 50 percent and most preferably less than about 10 percent.

The polymers are selected from a variety of natural, synthetic, and biosynthetic polymers that are biocompatible or biodegradable. A polymer based on a C—C backbone tends to resist degradation, whereas heteroatom-containing polymer backbones confer biodegradability. Biodegradability can, therefore, be engineered into polymers by the judicious addition of chemical linkages such as anhydride, ester, or amide bonds, among others. The usual mechanism for degradation is by hydrolysis or enzymatic cleavage of the labile heteroatom bonds, resulting in a scission of the polymer backbone. Macro organisms can eat and, sometimes, digest polymers, and also initiate a mechanical, chemical, or enzymatic aging. Biodegradable polymers with hydrolysable chemical bonds are researched extensively for biomedical, pharmaceutical, agricultural, and packaging applications. In order to be used in medical devices and controlled-drug-release applications, the biodegradable polymer must be biocompatible and meet other criteria to be qualified as biomaterial-processable, sterilizable, and capable of controlled stability or degradation in response to biological conditions. The chemical nature of the degradation products, rather than of the polymer itself, often critically influences biocompatibility. Poly(esters) based on polylactide (PLA), polyglycolide (PGA), polycaprolactone (PCL), and their copolymers have been extensively employed as biomaterials. Degradation of these materials yields the corresponding hydroxy acids, making them safe for in vivo use. Other bio- and environmentally degradable polymers include polyvinyl alcohols, poly(hydroxyalkanoate)s such as the polyhydroxybutyrate-polyhydroxyvalerate class, additional poly(ester)s, and natural polymers, particularly, modified poly(saccharide)s, e.g., starch, cellulose, and chitosan.

The rigidity of the scaffold containing discrete carbon nanotubes can be selected based on the choice of polymer, the ratio of polymer to discrete carbon nanotube and the density of the scaffold. The rigidity of the scaffold can determine the type of cell the stem cells differentiate towards.

Stem cells applied to this invention are not restricted, including any stem cell having inherent characteristics such as non-differentiation, infinite proliferation and differentiative potential to specific cells. The preferable stem cells used in this invention are classified into two groups: pluripotent stem cells such as embryonic stem cell and embryonic germ cell; and multipotent stem cells. Embryonic stem cells are derived from inner cell mass of blastocyst, and embryonic germ cells are derived from primordial germ cells present in 5-10 week aged gonadal ridge. Multipotent stem cells are found in embryonic tissues, fetus tissues or adult tissues, including adult (somatic) stem cells. Pluripotent stem cells are indefinitely proliferated in vitro and differentiate to three germ layers (ectoderm, mesoderm and endoderm). Unlikely, multipotent stem cells have capability to differentiate to their precursor tissues and their self-renewal potency is restricted. The source of multipotent stem cells includes any type of tissues, in particular, bone marrow, blood, liver, skin, intestine, spleen, brain, skeletal muscle and dental pulp.

Preferably, stem cells used in this invention are embryonic stem cell, adult stem cell, embryonic germ cell and embryonic carcinoma cell, more preferably, embryonic stem cell and adult stem cell.

Preferably, the cell therapy composition of this invention further comprises inducers for stem cell differentiation. Preferable example of the inducer comprises retinoic acid, ascorbic acid, melatonine and various growth factors [e.g., GDNF (glial cell line-derived neurotrophic factor), EGF (epidermal growth factor), NGF (nerve growth factor)]. The inducers for stem cell differentiation can be associated with the external or internal surfaces of the discrete carbon nanotubes. Most preferably the inducers for stem cell differentiation are released from the surfaces of the discrete carbon nanotubes in a controlled time-release manner. An example of controlled time release is to place the inducers for stem cell differentiation within the open ended discrete carbon nanotube and allow release through diffusion of the inducer molecules. Another method is to encapsulate the discrete carbon nanotubes and inducer molecules within a biocompatible or biodegradable material such as polylactic-glycolic acid. The inducer molecule can either diffuse through the biocompatible material or be released as the material biodegrades. Many other methods of controllably time releasing a wide variety of substances are known in the art and incorporated herein.

The stem cell scaffold described herein can further comprise fibers, films, platelets, or spherical particles, or combinations thereof.

The stem cell scaffold comprising discrete carbon nanotubes can further comprise other additives conducive for directing stem cell differentiation such as other inorganic types like graphite, graphene, and silicate structures, polymeric additives (polypropylene, polyethylene to name just a couple), and natural products such as silk or DNA strands.

The stem cell scaffold can have about 0.1% to 100% (volume) discrete carbon nanotubes, preferably greater than about 5%, more preferably greater than about 10%, most preferably greater than about 50%, and especially greater than about 95%, of the discrete carbon nanotubes.

The stem cell scaffold can comprise discrete carbon nanotubes wherein the lengths of the discrete carbon nanotubes can be a unimodal distribution, or a multimodal distribution (such as a bimodal distribution). The multimodal distributions can have evenly distributed ranges of lengths (such as 50% of one length range and about 50% of another length range). The distributions can also be asymmetrical—meaning that a relatively small percent of discrete nanotubes can have a specific length while a greater amount can comprise another length.

The stem cell scaffold can comprise discrete carbon nanotubes wherein the diameters of the discrete carbon nanotubes can be a unimodal distribution, or a multimodal distribution (such as a bimodal distribution). The multimodal distributions can have evenly distributed ranges of diameters (such as 50% of one diameter range and about 50% of another diameter range). The distributions can also be asymmetrical—meaning that a relatively small percent of discrete nanotubes can have a specific diameter while a greater amount can comprise another diameter.

The stem cell scaffold can comprise discrete carbon nanotubes wherein the discrete carbon nanotubes can comprise combinations of functionality. An example is a portion of discrete carbon nanotubes having 2% by weight of carboxylic acid groups are admixed with a portion of discrete carbon nanotubes having 2% by weight amine groups for the purpose of forming a network of discrete carbon nanotubes as a stem cell scaffold structure. Another example is a portion of discrete carbon nanotubes contacted with an anionic surfactant that are admixed with a portion of discrete carbon nanotubes contacted with a cationic surfactant for the purpose of forming a network of discrete carbon nanotubes as a stem cell scaffold structure. The carbon nanotubes can be contacted with an anionic, cationic or non-ionic surfactant. An example of an anionic surfactant is sodium dodecylsulfate. An example of a cationic surfactant is cetyltrimethylbromide. An example of a non-ionic surfactant is Pluronic F127, a block polyethylene oxide-polypropylene oxide.

The scaffold for transplanting stem cell comprising DCNT shows excellent scaffold properties in networking between differentiated stem cells and surrounding cells. The DCNT stem cell scaffold exhibits improved cell adhesiveness to improve cell density and cell-to cell adhesion, and no cytotoxicity. Such feature of DCNT contributes to the formation of networking between stem cells transplanted and surrounding tissues, allowing stem cells transplanted to exert their functions and effects. Furthermore, such feature prevents stem cells transplanted to be washed away.

In particular, the mixture for transplanting stem cells comprising DCNT can be easily transplanted in a fluid form, for example using a syringe. The stem cells can be surrounded by a dispersion of discrete carbon nanotubes to protect the stem cell during fluid transport, for example using an ink jet printer.

Furthermore, the scaffold of this invention promotes electric/physiological actions of cells unlike to silicone. In addition to this, DCNT used in this invention has some advantages in the senses that it reduces inflammatory responses (Shvedova A A, et al., Am. 1. Physiol Lung Cell Mol Physiol, 2005, November; 289(5):L698-708. Epub 2005 Jun. 10.).

Since DCNT is well mixed with stem cells and injected into sites of interest, it can decrease adverse effects associated with surgical procedures. The injected DCNT may form structures suitable in the formation of cell-to-cell networks over time. The electric conductivity of DCNT permits it to be delivered to sites of interest via electric induction, thereby making it possible to serve as stem cell scaffolds at sites with disrupted tissues.

The diseases or disorders treated by the present composition comprise all diseases or disorders that can be treated by stem cell therapy. Preferably, the cell therapy composition of this invention is applied to the treatment of neuronal diseases, cardiac ischemic injury or cardiomyopathy, injury of spinal column and degenerative rhinitis. According to a preferred embodiment, the stem cell contained in this invention is neuronal stem cell and the composition is one for treating neuronal diseases.

Where the cell therapy composition is used to treat neuronal diseases, the diseases includes any neuronal diseases caused by damage of neuronal cells. Preferably, the neuronal disease is selected from the group consisting of neurodegenerative disorder. More preferably, the neurodegenerative disorder is selected from the group consisting of Alzheimer's disease, Huntington's disease, Parkinson's disease, neuronal motor disease and amyotrophic lateral sclerosis, most preferably, Parkinson's disease.

Since the scaffold for transplanting stem cell comprising DCNT is easily transplanted as carbon nanoparticles with stem cells using syringe, it is preferable that the cell therapy composition of this invention comprises discrete carbon nanotubes in the form of a suspension.

The suitable amount of DCNT in the cell therapy composition is in the range of 0.002-60 mg/ml, preferably, 0.01-10 mg/ml, more preferably, 0.01-1 mg/ml, and most preferably 0.01-0.3 mg/ml.

In the cell therapy compositions of this invention, a pharmaceutically acceptable carrier may be conventional for formulation, including carbohydrates (e.g., lactose, amylose, dextrose, sucrose, sorbitol, mannitol, starch, cellulose), gum acacia, calcium phosphate, alginate, gelatin, calcium silicate, microcrystalline cellulose, polyvinylpyrrolidone, water, salt solutions, alcohols, gum arabic, syrup, vegetable oils (e.g., corn oil, cotton-seed oil, peanut oil, olive oil, coconut oil), polyethylene glycols, methyl cellulose, methylhydroxy benzoate, propylhydroxy benzoate, talc, magnesium stearate and mineral oil, but not limited to the pharmaceutical compositions of this invention, further may contain wetting agent, lubricant, stabilizer, or mixtures of these substances. Details of suitable pharmaceutically acceptable carriers and formulations can be found in Reminglon's Pharmaceutical Sciences (19th ed., 1995), which is incorporated herein by reference.

The correct dosage of the pharmaceutical compositions of this invention will be varied according to the particular formulation, the mode of application, age, body weight, and gender of the patient, diet, time of administration, route of administration, condition of the patient, excretion rate, reaction sensitivity and so on.

According to conventional techniques known to those skilled in the art, the cell therapy compositions of this invention can be formulated with pharmaceutical acceptable carrier and/or vehicle, finally providing several forms including a unit dosage form or a multi-unit dosage forms. The dosage forms can comprise a solution, a suspension or an emulsion in an oily or aqueous medium as well as further dispersions or stabilizers.

The cell therapy composition of this invention promotes the formation of networking between stem cells transplanted and surrounding tissues, allowing stem cells transplanted to fully exert their functions and effects.

Other aspects of the invention involving discrete carbon nanotubes in a scaffolding application include a controlled drug delivery system comprising MR or DCNT and at least one active drug ingredient, preferably wherein the active drug ingredient is substantially within the volume of the MR or DCNT, including such scaffolding that further comprises a substance attached to MR or DCNT that targets specific sites in the body (e.g., protein). The controlled drug delivery method can be activated by radiation such as electro-magnetic radiation, heat or ultraviolet radiation (e.g., magnetic resonance imaging, MRI).

Another aspect of the scaffolding application is a bone adhesive composition comprising MR or DCNT and a biocompatible adhesive (e.g., polyvinylalcohol (PVA), calcium phosphates, or polyurethanes), preferably activated by electro-magnetic radiation (e.g., MRI).

Structural bone systems and compositions comprising MR or DCNT, nerve repair comprising MR or DCNT and a biocompatible covering of MR or DCNT are also within the purview of the invention. These systems and compositions can be activated by radiation such as electro-magnetic radiation, x-rays, infra-red or ultraviolet radiation.

In addition to scaffolding, the invention also includes a stem cell growth and/or delivery substrate comprising MR or DCNT.

The discrete carbon nanotube scaffold can also comprise a foam or cellular structure.

The discrete carbon nanotube scaffold can also comprise a film or fiber.

The film, fiber or foam structures comprising discrete carbon nanotubes may also comprise layers differing in composition. For example, in a tape the layers may consist of different amounts of discrete carbon nanotubes, different types of discrete carbon nanotubes, or different additives or concentration of additives.

A useful method for differentiating stem cells may include first putting the stem cells in or on a chosen scaffold comprising discrete carbon nanotubes, such as a tape, culturing the stem cells to create the desired type of differentiated cell growth, then transplanting the differentiated cells into the living entity.

In various embodiments, a plurality of carbon nanotubes is disclosed comprising single wall, double wall or multi wall carbon nanotube fibers having an aspect ratio of from about 10 to about 500, preferably from about 40 to about 200, and an overall (total) oxidation level of from about 1 weight percent to about 15 weight percent, preferably from about 1 weight percent to about 10 weight percent, more preferably from about 1 weight percent to 5 weight percent, more preferably from about 1 weight percent to 3 weight percent. The oxidation level is defined as the amount by weight of oxygenated species covalently bound to the carbon nanotube divided by the total weight mass of oxygenated nanotubes. The thermogravimetric method for the determination of the percent weight of oxygenated species on the carbon nanotube involves taking about 7-15 mg of the dried oxidized carbon nanotube and heating at 5° C./minute from 100 degrees centigrade to 700 degrees centigrade in a dry nitrogen atmosphere. The percentage weight loss from 200 to 600 degrees centigrade is taken as the percent weight loss of oxygenated species. The oxygenated species can also be quantified using Fourier transform infra-red spectroscopy, FTIR, particularly in the wavelength range 1730-1680 $cm^{-1}$.

The carbon nanotubes can have oxidation species comprising carboxylic acid or derivative carbonyl containing species and are essentially discrete individual nanotubes, not entangled as a mass. Typically, the amount of discrete carbon nanotubes after completing the process of oxidation and shear is by a far a majority (that is, a plurality) and can be as high as 70, 80, 90 or even 99 percent of discrete carbon nanotubes, with the remainder of the tubes still partially entangled in some form. Complete conversion (i.e., 100 percent) of the nanotubes to discrete individualized tubes is most preferred. The derivative carbonyl species can include phenols, ketones, quaternary amines, amides, esters, acyl halogens, carboxylic groups, hydroxyl groups, monovalent metal salts and the like, and can vary between the inner and outer surfaces of the tubes. For example, one type of acid can be used to oxidize the tubes exterior surfaces, followed by water washing and induced shear, thereby breaking and separating the tubes. If desired, the formed discrete tubes, having essentially no (preferably <0.5%, more preferably zero) interior tube wall oxidation can be further oxidized with a different oxidizing agent, or even the same oxidizing agent as that used for the tubes' exterior wall surfaces at a different concentration, resulting in differing amounts—and/or differing types—of interior and surface oxidation.

In certain embodiments the interior surface oxidized species content may be different from the exterior surface oxidized species content by greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, greater than 99%, or 100% greater. In other embodiments, the interior surface oxidized species content may be different from the exterior surface oxidized species content by less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, less than 100%.

In further embodiments, the exterior surface oxidized species content may be different from the interior surface oxidized species content by greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, greater than 99%, or 100% greater. In other embodiments, the exterior surface oxidized species content may be different from the interior surface oxidized species content by less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, less than 100%.

In some embodiments, the discrete carbon nanotubes with an average length of 900 nm, outside diameter of 10-15 nm and inside diameter of 3-6 nm, can have about 0.1 mMoles/g to about 0.4 mMoles/g tubes carboxylic groups (COOH). The concentration of OH groups can be from about 0.1 mMoles/g to about 0.4 mMoles/g and the concentration of lactones can be from about 0.05 mMoles/g to about 0.3 mMoles/g. The total surface area can be from 200 $m^2$/g to 280 $m^2$/g. The bulk conductivity of a dried pressed mat of the discrete tubes can have be from about 1 to 6 ohms. The density of the discrete tubes can be 1.8 to 1.9 g/$cm^2$.

General Process to Make Discrete Carbon Nanotubes (DCNT) or Molecular Rebar (MR)

As manufactured carbon nanotubes in the form of fibrous bundles or granules can be obtained from different sources to make discrete carbon nanotubes. However, for the examples used herein, entangled carbon nanotubes obtained from CNano, grade Flotube 9000 are used. Flotube 9000 carbon nanotubes have less than 5% by weight of impurities of which about 4% by weight or less are residual catalyst. The number of walls which make up the carbon nanotube is about 10. The tube diameter distribution is about 13 nm (a later table herein lists other tube diameters of about 12.5 nm) by scanning electron microscopy (SEM). Carbon nanotube manufacturers can have higher percentage impurities and much broader and larger diameter tube distributions depending on manufacturing technique. The carbon nanotube diameter and diameter distributions are determined by and characteristic of the process and catalyst conditions used to make the carbon nanotubes. Other carbon nanotube manufacturers include Arkema and Southwest Nanotechnologies.

Resulting discrete carbon nanotube length and length distributions from the process of making MR are related in part to the initial catalyst efficiency and process conditions for the entangled or bundled carbon nanotubes. The MR process cuts the entangled or bundled carbon nanotubes preferentially at a catalyst site, or large concentration of Stones-Wales defects. The larger diameter carbon nanotubes are generally more difficult to cut and so longer discrete carbon nanotubes resulting from the MR process tend to have larger diameters. Preferably, substantially all of the ends of the discrete carbon nanotubes are open after the MR conversion process.

Method to Make Discrete CNT

Nitric acid solution (greater than about 60 weight % concentration, preferably above 65% nitric acid concentration, in water) in conjunction with a controlled high energy dispersive mixer is used to exfoliate the carbon nanotubes. Alternate oxidation methods such as mixed acid systems (e.g., nitric and sulfuric) can be used, but the single acid system improves subsequent filtration and control of oxidation rate, which in turn improves the operability of the process. The use of nitric acid is also preferred because of its low viscosity (1 centipoise at room temperature) that allows higher concentrations of carbon nanotubes to be employed.

One illustrative process for making discrete carbon nanotubes follows: A 16 liter mixture of 1.2% by weight of CNT's (obtained from CNano, grade Flotube 9000) in >65% nitric acid, is pumped at 1.5 l/min. thru a 1000 watt Heilsher cell using a 34 mm diameter sonitrode. The back pressure is 30 psi, the amplitude is set at 85% and the recorded watts are at 500-600. After all of the 16 liters are pumped through the cell, the CNT slurry is drained back and the process is repeated until the CNT's are exfoliated to the desired specification, for example as tested by optical microscopy and/or UV absorption. The degree of oxidation can be measured by several tests such as O1s spectroscopy, energy dispersive X-ray and thermo-gravimetric analysis.

The acid and discrete carbon nanotube mixture is then filtered and washed to pH greater than 3. Quantification of carboxylic and hydroxyl groups can be determined by titration using a sodium hydroxide solution.

An example of measurements of the lengths of discrete carbon nanotubes made by varying the degree of oxidation and intensity of mixing is given in Table 1

TABLE 1

| | Lengths (nm) | | |
| --- | --- | --- | --- |
| | Condition 1 | Condition 2 | Condition 3 |
| Mean | 424 | 487 | 721 |
| Standard Error | 25.3 | 34.9 | 50 |
| Median | 407 | 417.0 | 672 |
| Standard Deviation | 177 | 281 | 315 |
| Sample Variance | 31461 | 79108 | 99418 |
| Kurtosis | −0.83 | 1.5 | −0.02 |
| Skewness | 0.03 | 1.2 | 0.64 |
| Range | 650 | 1270.0 | 1364 |
| Minimum | 85 | 85.0 | 161 |
| Maximum | 735 | 1355 | 1525 |

Condition 1 is an example of a narrow distribution with low mean length. Condition 2 is an example of broad distribution with low mean length. Condition 3 is an example of high mean length and broad distribution.

Additives can be included and can further react or be completely inert with other components of the formulation. Fibrous additives can be surface active to react with surroundings. To determine tube lengths, a sample of tubes is diluted in isopropyl alcohol and sonicated for 30 minutes. It is then deposited onto a silica wafer and images are taken at 15 kV and 20,000× magnification by SEM. Three images are taken at different locations. Utilizing the JEOL software (included with the SEM) a minimum of 2 lines are drawn across on each image and measure the length of tubes that intersect this line.

Skewness is a measure of the asymmetry of a probability distribution. A positive value means the tail on the right side of the distribution histogram is longer than the left side and vice versa. Positive skewness is preferred which indicates means more tubes of long lengths. A value of zero means a relatively even distribution on both sides of the mean value. Kurtosis is the measure of the shape of the distribution curve and is generally relative to a normal distribution. Both skewness and kurtosis are unitless.

The following table shows representative values of discrete carbon nanotubes diameters:

TABLE 2

| Diameter (unrelated to condition above) | |
| --- | --- |
| Mean diameter (nm*) | 12.5 |
| Median diameter (nm) | 11.5 |
| Kurtosis | 3.6 |
| Skewness | 1.8 |

Calculated tube contour length aspect ratio for conditions 1, 2 and 3 are 34, 39, and 58, respectively.
*nm = nanometer The carbon nanotubes can have oxidation species comprising carboxylic acid or derivative carbonyl containing species and are essentially discrete individual nanotubes, not entangled as a mass. Typically, the amount of discrete carbon nanotubes after completing the process of oxidation and shear is by a far a majority (that is, a plurality) and can be as high as 70, 80, 90 or even 99 percent of discrete carbon nanotubes, with the remainder of the tubes still partially entangled in some form. Complete conversion (i.e., 100 percent) of the nanotubes to discrete individualized tubes is most preferred. The derivative carbonyl species can include phenols, ketones, quaternary amines, amides, esters, acyl halogens, carboxylic groups, hydroxyl groups, monovalent metal salts and the like, and can vary between the inner and outer surfaces of the tubes. For example, one type of acid can be used to oxidize the tubes exterior surfaces, followed by water washing and induced shear, thereby breaking and separating the tubes. If desired, the formed discrete tubes, having essentially no (preferably <0.5%, more preferably zero) interior tube wall oxidation can be further oxidized with a different oxidizing agent, or even the same oxidizing agent as that used for the tubes' exterior wall surfaces at a different concentration, resulting in differing amounts—and/or differing types—of interior and surface oxidation.

In certain embodiments the interior surface oxidized species content may be different from the exterior surface oxidized species content by greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, greater than 99%, or 100% greater. In other embodiments, the interior surface oxidized species content may be different from the exterior surface oxidized species content by less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, less than 100%.

In further embodiments, the exterior surface oxidized species content may be different from the interior surface oxidized species content by greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, greater than 99%, or 100% greater. In other embodiments, the exterior surface oxidized species content may be different from the interior surface oxidized species content by less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, less than 100%.

In some embodiments, the discrete carbon nanotubes with an average length of 900 nm, outside diameter of 10-15 nm and inside diameter of 3-6 nm, can have about 0.1 mMoles/g to about 0.4 mMoles/g tubes carboxylic groups (COOH). The concentration of OH groups can be from about 0.1 mMoles/g to about 0.4 mMoles/g and the concentration of lactones can be from about 0.05 mMoles/g to about 0.3 mMoles/g. The total surface area can be from 200 $m^2$/g to 280 $m^2$/g. The bulk conductivity of a dried pressed mat of the discrete tubes can have be from about 1 to 6 ohms. The density of the discrete tubes can be 1.8 to 1.9 g/$cm^2$.

General Process to Produce Discrete Carbon Nanotubes Having Targeted Oxidation

A mixture of 0.5% to 5% carbon nanotubes, preferably 3%, by weight is prepared with CNano grade Flotube 9000 carbon nanotubes and 65% nitric acid. While stirring, the acid and carbon nanotube mixture is heated to 70 to 90 degrees C. for 2 to 4 hours. The formed oxidized carbon nanotubes are then isolated from the acid mixture. Several methods can be used to isolate the oxidized carbon nanotubes, including but not limited to centrifugation, filtration, mechanical expression, decanting and other solid—liquid separation techniques. The residual acid is then removed by washing the oxidized carbon nanotubes with an aqueous medium such as water, preferably deionized water, to a pH of 3 to 4. The carbon nanotubes are then suspended in water at a concentration of 0.5% to 4%, preferably 1.5% by weight. The solution is subjected to intensely disruptive forces generated by shear (turbulent) and/or cavitation with process equipment capable of producing energy densities of $10^6$ to $10^8$ Joules/$m^3$. Equipment that meet this specification includes but is not limited to ultrasonicators, cavitators, mechanical homogenizers, pressure homogenizers and microfluidizers (Table 4). One such homogenizer is shown in U.S. Pat. No. 756,953, the disclosure of which is incorporated herein by reference. After shear processing, the oxidized carbon nanotubes are discrete and individualized carbon nanotubes. Typically, based on a given starting amount of entangled as-received and as-made carbon nanotubes, a plurality of discrete oxidized carbon nanotubes results from this process, preferably at least about 60%, more preferably at least about 75%, most preferably at least about 95% and as high as 100%, with the minority of the tubes, usually the vast minority of the tubes remaining entangled, or not fully individualized.

Another illustrative process for producing discrete carbon nanotubes follows: A mixture of 0.5% to 5% carbon nanotubes, preferably 3%, by weight is prepared with CNano Flotube 9000 grade carbon nanotubes and an acid mixture that consists of 3 parts by weight of sulfuric acid (97% sulfuric acid and 3% water) and 1 part by weight of nitric acid (65-70 percent nitric acid). The mixture is held at room temperature while stirring for 3-4 hours. The formed oxidized carbon nanotubes are then isolated from the acid mixture. Several methods can be used to isolate the oxidized carbon nanotubes, including but not limited to centrifugation, filtration, mechanical expression, decanting and other solid—liquid separation techniques. The acid is then removed by washing the oxidized carbon nanotubes with an aqueous medium, such as water, preferably deionized water, to a pH of 3 to 4. The oxidized carbon nanotubes are then suspended in water at a concentration of 0.5% to 4%, preferably 1.5% by weight. The solution is subjected to intensely disruptive forces generated by shear (turbulent) and/or cavitation with process equipment capable of producing energy densities of $10^6$ to $10^8$ Joules/m$^3$. Equipment that meet this specification includes but is not limited to ultrasonicators, cavitators mechanical homogenizers, pressure homogenizers and microfluidizers (Table 4).

Minimal Acid Oxidation (MAO)

The present application discloses a novel method of manufacture of carbon nanotubes with minimal acid oxidation. Acid oxidation of carbon nanotubes as previously described in various Bosnyak et al. patents (e.g., U.S. Pat. Nos. 8,475,961, 8,993,161 and 9,065,132, the disclosures of each of which are incorporated herein by reference) and patent applications, is done by suspension of the carbon nanotubes in acid at concentrations from 2 to 4% CNT by weight in acid. After oxidation, the acid is removed by some means of solid/fluid separation such as filtration. The amount of acid removed ranges from 60% to 70% with about 30% to 40% becoming waste. Centrifugation can reduce the waste to 10%; however, centrifugation is an expensive and high maintenance process.

In the MAO process, the concentration of carbon nanotubes in the reaction process is increased. Using nitric acid (65% concentration) mixtures of high CNT concentration such as 43% CNT by weight in nitric acid has the unexpected consistency of a flowable powder. When the oxidation process is complete, the acid is not removed but diluted with water and then filtered during the washing process. This eliminates the step of acid filtration for retrieval of acid. The amount of acid wasted in the washing process is significantly less than in the process utilizing more acid with less nanotubes in the reaction.

Minimal acid oxidation (MAO) uses a wet powder process to eliminate excess acid. In MAO process the nitric acid (65% concentration) is mixed with the CNT to a concentration of 43.2% by weight CNT to acid. It is then subjected to heating to 90° C. The amount of oxidation and removal of metals is controlled by the time and temperature of reaction. Table 4 is an illustrative example. Note that the nitric acid waste, when utilizing the MAO process, is only 1.3 times the weight of the CNT as compared to 9.6 times the weight of the CNT with 70% acid removal efficiency or 3.2 time the weight of the CNT with 90% acid removal efficiency. This significantly reduces the cost of production by decreasing the amount of waste acid per mass of CNT, decreasing waste disposal and removing the filtration of acid step.

TABLE 3

|  | High Acid Method (Assuming 70% filter efficiency | High Acid Method (Assuming 90% filter efficiency | Minimal Acid method. |
|---|---|---|---|
| Reaction Mixture | 3 parts CNT to 97 part HNO3 by weight | 3 parts CNT to 97 part HNO3 by weight | 43 parts CNT to 56 parts HNO3 by weight |
| After filtration | 3 parts CNT to 29 parts HNO3 by weight | 3 parts CNT to 9.7 parts HNO3 by weight | Not Required |
| Acid lost due to water wash | 9.6 times the weight of CNT | 3.2 times the weight of CNT | 1.3 times the weight of CNT |

In addition to the waste saving, the MAO process removes the same amount of metal impurities from the tubes and the tube length, tube length distribution and detangling quality are the same as the higher acid method. In three scaled-up laboratory production runs, MAO resulted in a higher percentage oxidization of carbon nanotubes compared to the high acid method (2.59, 2.99, 4.01% Ox with MAO v. 1.9% Ox with higher amount of acid). Thus, even with relatively inefficient laboratory mixing, MAO resulted in reproducible oxidation and by control of the temperature and time, the amount of oxidation and amount of residual metals removed is controlled. The carbon nanotubes produced by MAO have the same kinds of functionalities, and the increase in oxidation does not change the species but increases the amount mm/g functionality of each species. MAO provides advantages by eliminating acid filtration, reducing the amount of acid wasted, giving greater control of percent oxidation, achieving increased oxidation and reducing residue in less time. The increased oxidation in MAO also enables further downstream chemistry modification.

In various embodiments, a plurality of carbon nanotubes is disclosed comprising single wall, double wall or multi wall carbon nanotube fibers having an aspect ratio of from about 10 to about 500, preferably from about 40 to about 200, and an overall (total) oxidation level of from about 1 weight percent to about 15 weight percent, preferably from about 1 weight percent to about 10 weight percent, more preferably from about 1 weight percent to 5 weight percent, more preferably from about 1 weight percent to 3 weight percent. The oxidation level is defined as the amount by weight of oxygenated species covalently bound to the carbon nanotube divided by the total weight mass of oxygenated nanotubes. The thermogravimetric method for the determination of the percent weight of oxygenated species on the carbon nanotube involves taking about 7-15 mg of the dried oxidized carbon nanotube and heating at 5° C./minute from 100 degrees centigrade to 700 degrees centigrade in a dry nitrogen atmosphere. The percentage weight loss from 200 to 600 degrees centigrade is taken as the percent weight loss of oxygenated species. The oxygenated species can also be quantified using Fourier transform infra-red spectroscopy, FTIR, particularly in the wavelength range 1730-1680 cm$^{-1}$.

The carbon nanotubes can have oxidation species comprising carboxylic acid or derivative carbonyl containing species and are essentially discrete individual nanotubes, not entangled as a mass. Typically, the amount of discrete carbon nanotubes after completing the process of oxidation and shear is by a far a majority (that is, a plurality) and can be as high as 70, 80, 90 or even 99 percent of discrete carbon nanotubes, with the remainder of the tubes still partially entangled in some form. Complete conversion (i.e., 100 percent) of the nanotubes to discrete individualized tubes is most preferred. The derivative carbonyl species can include phenols, ketones, quaternary amines, amides, esters, acyl halogens, carboxylic groups, hydroxyl groups, monovalent metal salts and the like, and can vary between the inner and outer surfaces of the tubes. For example, one type of acid can be used to oxidize the tubes exterior surfaces, followed by water washing and induced shear, thereby breaking and separating the tubes. If desired, the formed discrete tubes, having essentially no (preferably <0.5%, more preferably zero) interior tube wall oxidation can be further oxidized with a different oxidizing agent, or even the same oxidizing agent as that used for the tubes' exterior wall surfaces at a different concentration, resulting in differing amounts—and/or differing types—of interior and surface oxidation.

In certain embodiments the interior surface oxidized species content may be different from the exterior surface oxidized species content by greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, greater than 99%, or 100% greater. In other embodiments, the interior surface oxidized species content may be different from the exterior surface oxidized species content by less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, less than 100%.

In further embodiments, the exterior surface oxidized species content may be different from the interior surface oxidized species content by greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, greater than 99%, or 100% greater. In other embodiments, the exterior surface oxidized species content may be different from the interior surface oxidized species content by less than 20%, less than 25%, less than 30%, less than 35%, less than 40%, less than 45%, less than 50%, less than 55%, less than 60%, less than 65%, less than 70%, less than 75%, less than 80%, less than 85%, less than 90%, less than 95%, less than 100%.

In some embodiments, the discrete carbon nanotubes with an average length of 900 nm, outside diameter of 10-15 nm and inside diameter of 3-6 nm, can have about 0.1 mMoles/g to about 0.4 mMoles/g tubes carboxylic groups (COOH). The concentration of OH groups can be from about 0.1 mMoles/g to about 0.4 mMoles/g and the concentration of lactones can be from about 0.05 mMoles/g to about 0.3 mMoles/g. The total surface area can be from 200 m2/g to 280 m2/g. The bulk conductivity of a dried pressed mat of the discrete tubes can have be from about 1 to 6 ohms. The density of the discrete tubes can be 1.8 to 1.9 g/cm2.

After shear and/or cavitation processing, the oxidized carbon nanotubes become oxidized, discrete carbon nanotubes. Typically, based on a given starting amount of entangled as-received and as-made carbon nanotubes, a plurality of discrete oxidized carbon nanotubes results from this process, preferably at least about 60%, more preferably at least about 75%, most preferably at least about 95% and as high as 100%, with the minority of the tubes, usually the vast minority of the tubes remaining entangled, or not fully individualized.

EXAMPLE 1

Entangled Oxidized as MWCNT—3 Hour (oMWCNT-3)

One hundred milliliters of >64% nitric acid is heated to 85 degrees C. To the acid, 3 grams of as-received, multi-walled carbon nanotubes (C9000, CNano Technology) are added. The as-received tubes have the morphology of entangled balls of wool. The mixture of acid and carbon nanotubes are mixed while the solution is kept at 85 degrees for 3 hours and is labeled "oMWCNT-3". At the end of the reaction period, the oMWCNT-3 are filtered to remove the acid and washed with reverse osmosis (RO) water to pH of 3-4. After acid treatment, the carbon nanotubes are still entangled balls. The tubes are dried at 60° C. to constant weight.

EXAMPLE 2

Entangled Oxidized as MWCNT—6 Hour (oMWCNT-6)

One hundred milliliters of >64% nitric acid is heated to 85 degrees C. To the acid, 3 grams of as-received, multi-walled carbon nanotubes (C9000, CNano Technology) are added. The as-received tubes have the morphology of entangled balls of wool. The mixture of acid and carbon nanotubes are mixed while the solution is kept at 85 degrees for 6 hours and is labeled "oMWCNT-6". At the end of the reaction period, the oMWCNT-6 are filtered to remove the acid and washed with reverse osmosis (RO) water to pH of 3-4. After acid treatment, the carbon nanotubes are still entangled balls. The tubes are dried at 60° C. to constant weight.

EXAMPLE 3

Discrete Carbon Nanotube—Oxidize Outermost Wall (Out-DMWCNT)

In a vessel, 922 kilograms of 64% nitric acid is heated to 83° C. To the acid, 20 kilograms of as received, multi-walled carbon nanotubes (C9000, CNano Technology) is added. The mixture is mixed and kept at 83° C. for 3 hours. After the 3 hours, the acid is removed by filtration and the carbon nanotubes washed with RO water to pH of 3-4. After acid treatment, the carbon nanotubes are still entangled balls with few open ends. While the outside of the tube is oxidized forming a variety of oxidized species, the inside of the nanotubes have little exposure to acid and therefore little oxidization. The oxidized carbon nanotubes are then suspended in RO water at a concentration of 1.5% by weight. The RO water and oxidized tangled nanotubes solution is subjected to intensely disruptive forces generated by shear (turbulent) and/or cavitation with process equipment capable of producing energy densities of $10^6$ to $10^8$ Joules/m$^3$. The resulting sample is labeled "out-dMWCNT" which represents outer wall oxidized and "d" as discrete. Equipment that meet this shear includes but is not limited to ultrasonicators, cavitators, mechanical homogenizers, pressure homogenizers, and microfluidizers (Table 4). It is believed that the shear and/or cavitation processing detangles and discretizes the oxidized carbon nanotubes through mechanical means that result in tube breaking and opening of the ends due to breakage particularly at defects in the CNT structure which is normally a 6 member carbon rings. Defects happen at places in the tube which are not 6 member carbon rings. As this is done in water, no oxidation occurs in the interior surface of the discrete carbon nanotubes.

EXAMPLE 4

Discrete Carbon Nanotube—Oxidized Outer and Inner Wall (Out/In-DMWCNT)

To oxidize the interior of the discrete carbon nanotubes, 3 grams of the out-dMWCNT is added to 64% nitric acid heated to 85° C. The solution is mixed and kept at temperature for 3 hours. During this time, the nitric acid oxidizes the interior surface of the carbon nanotubes. At the end of 3 hours, the tubes are filtered to remove the acid and then washed to pH of 3-4 with RO water. This sample is labeled "out/in-dMWCNT" representing both outer and inner wall oxidation and "d" as discrete.

Oxidation of the samples of carbon nanotubes is determined using a thermogravimetric analysis method. In this example, a TA Instruments Q50 Thermogravimetric Analyzer (TGA) is used. Samples of dried carbon nanotubes are ground using a vibration ball mill. Into a tared platinum pan of the TGA, 7-15 mg of ground carbon nanotubes are added. The measurement protocol is as follows. In a nitrogen environment, the temperature is ramped from room temperature up to 100° C. at a rate of 10° C. per minute and held at this temperature for 45 minutes to allow for the removal of residual water. Next the temperature is increased to 700° C. at a rate of 5° C. per minute. During this process the weight percent change is recorded as a function of temperature and time. All values are normalized for any change associated with residual water removal during the 100° C. isotherm. The percent of oxygen by weight of carbon nanotubes (% Ox) is determined by subtracting the percent weight change at 600° C. from the percent weight change at 200° C.

A comparative table (Table 5 below) shows the levels of oxidation of different batches of carbon nanotubes that have been oxidized either just on the outside (Batch 1, Batch 2, and Batch 3), or on both the outside and inside (Batch 4). Batch 1 (oMWCNT-3 as made in Example 1 above) is a batch of entangled carbon nanotubes that are oxidized on the outside only when the batch is still in an entangled form (Table 5, first column). Batch 2 (oMWCNT-6 as made in Example 2 above) is also a batch of entangled carbon nanotubes that are oxidized on the outside only when the batch is still in an entangled form (Table 5, second column). The average percent oxidation of Batch 1 (2.04% Ox) and Batch 2 (2.06% Ox) are essentially the same. Since the difference between Batch 1 (three hour exposure to acid) and Batch 2 (six hour exposure to acid) is that the carbon nanotubes were exposed to acid for twice as long a time in Batch 2, this indicates that additional exposure to acid does not increase the amount of oxidation on the surface of the carbon nanotubes.

Batch 3 (Out-dMWCNT as made in Example 3 above) is a batch of entangled carbon nanotubes that were oxidized on the outside only when the batch was still in an entangled form (Table 5, third column). Batch 3 was then been made into a discrete batch of carbon nanotubes without any further oxidation. Batch 3 serves as a control sample for the effects on oxidation of rendering entangled carbon nanotubes into discrete nanotubes. Batch 3 shows essentially the same average oxidation level (1.99% Ox) as Batch 1 and Batch 2. Therefore, Batch 3 shows that detangling the carbon nanotubes and making them discrete in water opens the ends of the tubes without oxidizing the interior.

Finally, Batch 4 (Out/In-dMWCNT as made in this Example 4 herein) is a batch of entangled carbon nanotubes that are oxidized on the outside when the batch is still in an entangled form, and then oxidized again after the batch has then been made into a discrete batch of carbon nanotubes (Table 5, fourth column). Because the discrete carbon nanotubes are open ended, in Batch 4 acid enters the interior of the tubes and oxidizes the inner surface. Batch 4 shows a significantly elevated level of average oxidation (2.39% Ox) compared to Batch 1, Batch 2 and Batch 3. The significant elevation in the average oxidation level in Batch 4 represents the additional oxidation of the carbon nanotubes on their inner surface. Thus, the average oxidation level for Batch 4 (2.39% Ox) is about 20% higher than the average oxidation levels of Batch 3 (1.99% Ox). In Table 5 below, the average value of the oxidation is shown in replicate for the four batches of tubes. The percent oxidation is within the standard deviation for Batch 1, Batch 2 and Batch 3.

TABLE 4

| Homogenizer Type | Flow Regime | Energy Density (J·m$^{-3}$) |
|---|---|---|
| Stirred tanks | turbulent inertial, turbulent viscous, laminar viscous | $10^3$-$10^6$ |
| Colloid mil | laminar viscous, turbulent viscous | $10^3$-$10^8$ |
| Toothed - disc disperser | turbulent viscous | $10^3$-$10^8$ |
| High pressure homogenizer | turbulent inertial, turbulent viscous, cavitation inertial, laminar viscous | $10^6$-$10^8$ |
| Ultrasonic probe | cavitation inertial | $10^6$-$10^8$ |
| Ultrasonic jet | cavitation inertial | $10^6$-$10^8$ |
| Microfluidization | turbulent inertial, turbulent viscous | $10^6$-$10^8$ |
| Membrane and mircochannel | Injection spontaneous transformation based | Low $10^3$ |

Excerpted from *Engineering Aspects of Food Emulsification and Homogenization*, Ed. M Rayner and P. Dejmek, CRC Press, New York 2015

TABLE 5

Percent oxidation by weight of carbon nanotubes.

| Batch 1: oMWCNT-3 % Ox | Batch 2: oMWCNT-6 % Ox | Batch 3: Out-dMWCNT % Ox | Batch 4: Out/In-dMWCNT % Ox | Difference in % Ox (Batch 4 − Batch 3) | *% difference in % Ox (Batch 4 v Batch 3) |
|---|---|---|---|---|---|
| 1.92 | 1.94 | 2.067 | 2.42 | 0.353 | 17% |
| 2.01 | 2.18 | 1.897 | 2.40 | 0.503 | 26.5% |

TABLE 5-continued

Percent oxidation by weight of carbon nanotubes.

|  | Batch 1: oMWCNT-3 % Ox | Batch 2: oMWCNT-6 % Ox | Batch 3: Out-dMWCNT % Ox | Batch 4: Out/In-dMWCNT % Ox | Difference in % Ox (Batch 4 − Batch 3) | *% difference in % Ox (Batch 4 v Batch 3) |
|---|---|---|---|---|---|---|
|  | 2.18 | NM | 2.12 | 2.36 | 0.24 | 11% |
|  | 2.05 | NM | 1.85 | NM | n/a | n/a |
| Average | 2.04 | 2.06 | 1.99 | 2.39 | 0.4 | 20% |
| St. Dev. | 0.108 | 0.169 | 0.130 | 0.030 | n/a | n/a |

NM = Not Measured
*% difference between interior and exterior oxidation surfaces (Batch 4 v Batch 3) = (((outside % oxidation) − (inside % oxidation)) ÷ (outside % oxidation)) × 100

Method to Make a Stem Cell Scaffold.

A suspension of discrete carbon nanotubes, a biocompatible polymer and stem cells. Discrete carbon nanotubes (1 gram) having a length distribution of composition 3 and 2% by weight of oxidized species is admixed with water (98 grams) at room temperature and 1 gram of polyvinyl alcohol (Aldrich, 88% hydrolyzed, molecular weight 31-70 KDa). The pH of the mixture is adjusted to about pH 7 using sodium hydroxide. The mixture is sonicated in a sonicator bath for 30 minutes. 100 grams of a mixture of stem cells in water (approximately $1 \times 10^9$ cells per liter) is added to the discrete carbon nanotube mixture to form a stable mixture. The mixture can be deposited on glass surfaces to culture growth of differentiated stem cells. The mixture can also be placed within an animal via hypodermic syringe. Once the mixture has settled following being placed via hypodermic syringe or another method of placement, if the mixture remains in substantially the same location, it will be considered to not have moved from where it was placed. In some embodiments, less than about 10% of the mixture will move significantly from where it was placed, in others less than about 5%, in others less than about 3%, and in still other embodiments less than about 1% of the mixture will move significantly from where it was placed. Depending on the composition of the mixture, the location of placement, and the circumstances surrounding placement, significant movement may indicate movement greater than 10 centimeters, or greater than 5 centimeters, or greater than 3 centimeters, or greater than 1 centimeter, or greater than 5 millimeters, or greater than 1 millimeter.

A Method to Include a Medicament.

Discrete carbon nanotubes with a portion of open ends are washed to pH 6 and dried in vacuo for 4 hours at 80 degrees centigrade. (1 g) of the dried discrete carbon nanotubes are added to anhydrous ethanol (100 g) containing 0.05 g of retinoic acid (also known as vitamin A acid). The mixture is sonicated for 30 minutes at 50 degrees centigrade then cooled to room temperature. The discrete carbon nanotubes with adsorbed retinoic acid are filtered and dried. 1 gram of the discrete carbon nanotubes with retinoic acid are mixed with 98 grams of water at pH about 7 and 1 gram of polyvinyl alcohol (Aldrich, 88% hydrolyzed, molecular weight 31-70 KDa) at room temperature and sonicated in a water bath for 30 minutes to obtain a stable dispersion of discrete carbon nanotubes containing retinoic acid. 100 grams of a mixture of stem cells in water (approximately $1 \times 10^9$ cells per liter) is added to the discrete carbon nanotube containing retinoic acid mixture. The mixture can be deposited on glass surfaces to culture growth of differentiated stem cells. The mixture can also be placed within an animal via hypodermic syringe.

Embodiments

Specific embodiments disclosed herein include:
1. A scaffold for transplanting a stem cell, which comprises discrete carbon nanotubes; wherein the scaffold does not exhibit cytotoxicity.
2. The scaffold of embodiment 1, wherein the discrete carbon nanotubes comprise an amount of functional groups of at least about 1 percent by weight of the dry discrete carbon nanotubes.
3. The scaffold of embodiment 1 wherein a plurality of the discrete carbon nanotubes are open ended.
4. The scaffold of embodiment 1 wherein a plurality of the discrete carbon nanotubes are substantially cleaned of catalytic residues.
5. The scaffold of embodiment 1 wherein a plurality of the discrete carbon nanotubes have a length less than 4 micrometers, preferably less than 3 micrometers and more preferably less than 2 micrometers.
6. The scaffold of embodiment 5 wherein a plurality of the discrete carbon nanotubes have a length distribution modality, preferably bimodal.
7. The scaffold of embodiment 1 further comprising a polymer.
8. The scaffold of embodiment 7 wherein the polymer is selected from a group of polymers that do not exhibit cytotoxicity.
9. The scaffold of embodiment 7 wherein the polymer is selected from a group of polymers that are biodegradable.
10. The scaffold of embodiment 7 wherein the polymer is selected from a group of polymers that are water soluble.
11. The scaffold of embodiment 1, wherein the discrete carbon nanotubes comprise functional groups that increase affinity of biological moieties to the discrete carbon nanotube surface.
12. A composition for stem cell therapy, which comprises: (a) a stem cell; and (b) discrete carbon nanotubes serving as a stem cell scaffold without cytotoxicity.
13. The composition according to embodiment 12, wherein the stem cell is embryonic stem cell or adult stem cell.
14. The composition according to embodiment 12, wherein the stem cell is neuronal stem cell and the composition is one for treating neuronal diseases.
15. The composition according to embodiment 14, wherein the neuronal disease is selected from the group consisting of neurodegenerative disorder.
16. The composition according to embodiment 15, wherein the neurodegenerative disorder is selected from the group consisting of Alzheimer's disease, Huntington's disease, Parkinson's disease, motor neuron disease and amyotrophic lateral sclerosis.
17. The composition according to embodiment 12, wherein the discrete carbon nanotube is in the form of suspension.
18. The composition according to embodiment 12, wherein the composition can be deposited in a body tissue such that the composition does not move from where it was placed
19. The composition according to embodiment 12, wherein the composition can be deposited to form three dimensional shapes that can be stable and that can form tissues to repair damaged or missing body tissues and parts.
20. The composition according to embodiment 12, wherein the discrete carbon nanotube may be incorporated into the body tissue as part of the body tissue
21. The composition according to embodiment 12, wherein the composition can be detected by electromagnetic fields to determine the positioning of the composition
22. The composition according to embodiment 12, wherein the composition can contain antibiotics or pain medications or growth stimulants that can be slowly released to help tissue growth.
23. A cell therapy method using a stem cell, which comprises administering to an animal a composition for stem cell therapy comprising (a) a stem cell; and (b) discrete carbon nanotubes serving as a stem cell scaffold without cytotoxicity.
24. The cell therapy method according to embodiment 18, wherein the stem cell is embryonic stem cell or adult stem cell.
25. The cell therapy method according to embodiment 18, wherein the stem cell is neuronal stem cell and the composition is one for treating neuronal diseases.
26. The cell therapy method according to embodiment 20, wherein the neuronal disease is selected from the group consisting of neurodegenerative disorder.
27. The cell therapy method according to embodiment 18, wherein the neurodegenerative disorder is selected from the group consisting of Alzheimer's disease, Huntington's disease, Parkinson's disease, motor neuron disease and amyotrophic lateral sclerosis.
28. The cell therapy method according to embodiment 18, wherein the ischemia-reperfusion injury is ischemic stroke.
29. The cell therapy method according to embodiment 18, wherein the discrete carbon nanotube is in the form of suspension.
30. Use of a composition comprising (a) a stem cell; and (b) discrete carbon nanotubes serving as a stem cell scaffold without cytotoxicity for manufacturing a medicament for cell therapy.
31. The use according to embodiment 25, wherein the stem cell is embryonic stem cell or adult stem cell.
32. The use according to embodiment 25, wherein the stem cell is neuronal stem cell and the composition is one for treating neuronal diseases.
33. The use according to embodiment 27, wherein the neuronal disease is selected from the group consisting of neurodegenerative disorder.
34. The use according to embodiment 28, wherein the neurodegenerative disorder is selected from the group consisting of Alzheimer's disease, Huntington's disease, Parkinson's disease, neural motor disease and amyotrophic lateral sclerosis.
35. The use according to embodiment 25, wherein the discrete carbon nanotubes are in the form of suspension.
36. The composition of embodiment 12 wherein the scaffold and stem cell for stem cell therapy further comprise a medicant.
37. The composition of embodiment 12 wherein the scaffold is in the form of a foam, fiber or film.
38. The composition of embodiment 12 wherein the scaffold comprises a multilayer.
39. The scaffold of embodiment 1 wherein a least a portion of the discrete carbon nanotubes are oriented.
40. The scaffold of embodiment 7, wherein the polymer comprises a weight percentage range of about 1 to about 99, preferably less than about 90 percent, more preferably less than about 50 percent and most preferably less than about 10 percent of the scaffold.
41. A method to protect stem cells from damage by encasing the stem cell into a scaffold comprising discrete carbon nanotubes.
42. A method to protect stems cells from damage during injection or deposition by encasing the stem cell into a scaffold comprising discrete carbon nanotubes.
43. The composition of embodiment 12 further comprising an inducer for stem cell differentiation.
44. A method to form a scaffold by admixing a mixture of discrete nanotubes with different functionalities, wherein on mixing the nanotubes associate with each other type of functionality.
45. The scaffold of embodiment 1 further comprising a surfactant.
46. The scaffold of embodiment 1 used as an adhesive for tissue, or bone.
47. The scaffold of embodiment 7, wherein the polymer is selected from a group of biological polymers consisting of proteins, peptides, long chain carbohydrates, proteoglycans, and lipids.
48. The scaffold of embodiment 43 wherein the polymer is partly digested or modified.
49. The scaffold of embodiment 43 which has components substantially similar to the make-up of the extracellular matrix.
50. The scaffold of embodiment 43 wherein the polymer is an antibody locking the scaffold to lesions or sites of cell damage.
51. The scaffold of embodiment 43 wherein the biopolymer is selected from a group consisting of chemotactic, wound healing, extracellular matrix producing proteins, comprising fibronectin, integrin, or fibrin.
52. The scaffold of embodiment 43 wherein the polymer is retrieved from the patient to shield the scaffold from immunological attack.
53. The scaffold of embodiment 48 wherein the polymer is selected from a group of proteins consisting of albumin, alpha-fetoglobulin, and alpha-albumin.
54. The composition of embodiment 12 wherein the stem cells used are grown using tissue samples from the patient (personalized medicine).
55. The composition of embodiment 12 wherein the stem cells are differentiated prior to implantation.
56. The scaffold of Embodiment 1, wherein the discrete carbon nanotubes comprise an interior and exterior surface, each surface comprising an interior surface oxidized species content and an exterior surface oxidized species content.

57. The composition of Embodiment 57 wherein the interior surface oxidized species content is less than the exterior surface oxidized species content.
58. The composition of Embodiment 57, wherein the interior surface oxidized species content is greater than the exterior surface oxidized species content.
59. The composition of Embodiment 57, wherein the interior surface oxidized species content is at least 99% greater than the exterior surface oxidized species content.
60. The composition of Embodiment 57, wherein the exterior surface oxidized species content is at least 99% greater than the interior surface oxidized species content.
61. The composition of Embodiment 57, wherein the interior and exterior surface oxidized species content totals from about 57 to about 9 weight percent based on carbon nanotube weight, the discrete carbon nanotubes comprise a plurality of open ended tubes.
62. The composition of Embodiment 57, wherein the discrete carbon nanotubes are multiwalled carbon nanotubes.
63. The composition of Embodiment 57, wherein the oxidized species is selected from the group consisting of carboxylic acids, phenols, aldehydes, ketones, hydroxyl, carboxylic, ether linkages, and combinations thereof.
64. The composition of Embodiment 57, wherein the total oxidized species content of the interior surface and exterior surface comprises from about 1% to 15% by weight of the carbon nanotubes.

The above description is for the purpose of teaching the person of ordinary skill in the art how to practice the present application, and it is not intended to detail all those obvious modifications and variations of it which will become apparent to the skilled worker upon reading the description. It is intended, however, that all such obvious modifications and variations be included within the scope of the present application, which is defined by the following claims. The claims are intended to cover the claimed components and steps in any sequence which is effective to meet the objectives there intended, unless the context specifically indicates the contrary.

What is claimed is:

1. A scaffold for transplanting a stem cell, which comprises discrete carbon nanotubes; wherein the scaffold does not exhibit cytotoxicity and wherein the discrete carbon nanotubes comprise an interior and exterior surface, the interior surface comprising an interior surface oxidized species content and the exterior surface comprising an exterior surface oxidized species content, and wherein the interior surface oxidized species content is less than the exterior surface oxidized species content.
2. The scaffold of claim 1, wherein the discrete carbon nanotubes comprise an amount of functional groups of at least about 1 percent by dry weight of the discrete carbon nanotubes.
3. The scaffold of claim 1 wherein a plurality of the discrete carbon nanotubes are open ended.
4. The scaffold of claim 1 wherein a plurality of the discrete carbon nanotubes are substantially cleaned of catalytic residues.
5. The scaffold of claim 1 further comprising a polymer.
6. The composition of claim 5 wherein the polymer is selected from the group consisting proteins, peptides, long chain carbohydrates, proteoglycans, and lipids.
7. The scaffold of claim 1, wherein the discrete carbon nanotubes comprise functional groups that increase the affinity of biological moieties to the discrete carbon nanotube surface.
8. The scaffold of claim 1 wherein the interior and exterior surface oxidized species content totals from about 1 to about 9 weight percent based on carbon nanotube weight.
9. The scaffold of claim 1 wherein the discrete carbon nanotubes comprise a plurality of open ended tubes.
10. The scaffold of claim 1, wherein the discrete carbon nanotubes are multiwalled carbon nanotubes.
11. The scaffold of claim 1 wherein the total oxidized species content of the interior surface and exterior surface comprises from about 1% to 15% by weight of the carbon nanotubes.
12. The scaffold of claim 1 wherein the scaffold is in the form of a foam, fiber, or film.
13. The scaffold of claim 1 further comprising a stem cell.
14. The scaffold of claim 1 further comprising a medicant.
15. The scaffold of claim 1 wherein the scaffold is in the form of a multilayer tape.
16. The scaffold of claim 1 wherein at least a portion of the discrete carbon nanotubes are oriented.
17. A composition for stem cell therapy, which comprises: (a) at least one stem cell; and (b) discrete carbon nanotubes serving as a stem cell scaffold without cytotoxicity and wherein the discrete carbon nanotubes comprise an interior and exterior surface, the interior surface comprising an interior surface oxidized species content and the exterior surface comprising an exterior surface oxidized species content, and wherein the interior surface oxidized species content is less than the exterior surface oxidized species content.
18. The composition according to claim 17, wherein the at least one stem cell comprises an embryonic stem cell, an adult stem cell, or a combination thereof.
19. The composition according to claim 17, wherein the at least one stem cell comprises a neuronal stem cell and the composition is one for treating neuronal diseases.
20. The composition according to claim 19, wherein the neuronal disease is selected from the group consisting of neurodegenerative disorders.
21. The composition according to claim 17, wherein the discrete carbon nanotubes are in the form of a suspension.
22. The composition according to claim 17, wherein the composition is deposited in a body tissue such that the composition does not move from where it was placed.
23. The composition according to claim 17, wherein the composition is deposited to form three dimensional shapes to repair body tissues or parts.
24. The composition according to claim 17, wherein the composition further comprises an antibiotic.
25. The composition of claim 17 further comprising a medicant.
26. A cell therapy method which comprises administering to an animal a composition for stem cell therapy comprising (a) at least one stem cell; and (b) discrete carbon nanotubes serving as a stem cell scaffold without cytotoxicity and wherein the discrete carbon nanotubes comprise an interior and exterior surface, the interior surface comprising an interior surface oxidized species content and the exterior surface comprising an exterior surface oxidized species content, and wherein the interior surface oxidized species content is less than the exterior surface oxidized species content.
27. The cell therapy method according to claim 26, wherein the at least one stem cell is a neuronal stem cell.

28. The cell therapy method according to claim 26, wherein the discrete carbon nanotubes are in the form of a suspension.

\* \* \* \* \*